US012402872B2

(12) United States Patent
Galbierz et al.

(10) Patent No.: US 12,402,872 B2
(45) Date of Patent: Sep. 2, 2025

(54) CONVERTIBLE TISSUE RETRACTOR

(71) Applicant: GSQUARED MEDICAL LLC, Nashville, TN (US)

(72) Inventors: Thomas R. Galbierz, Brentwood, TN (US); Michael A. Galbierz, St. Louis, MO (US)

(73) Assignee: GSQUARED MEDICAL LLC, Brentwood, TN (US)

( * ) Notice: Subject to any disclaimer, the term of this patent is extended or adjusted under 35 U.S.C. 154(b) by 252 days.

(21) Appl. No.: 17/797,990

(22) PCT Filed: Feb. 19, 2021

(86) PCT No.: PCT/US2021/018837
§ 371 (c)(1),
(2) Date: Aug. 5, 2022

(87) PCT Pub. No.: WO2021/173447
PCT Pub. Date: Sep. 2, 2021

(65) Prior Publication Data
US 2023/0044918 A1    Feb. 9, 2023

Related U.S. Application Data

(60) Provisional application No. 62/981,377, filed on Feb. 25, 2020.

(51) Int. Cl.
*A61B 17/02* (2006.01)
*A61F 13/0246* (2024.01)
(Continued)

(52) U.S. Cl.
CPC .......... *A61B 17/02* (2013.01); *A61F 13/0253* (2013.01); *A61F 13/05* (2024.01);
(Continued)

(58) Field of Classification Search
CPC ......... A61F 13/0253; A61B 2017/0212; A61B 17/02; A61B 2017/0225
See application file for complete search history.

(56) References Cited

U.S. PATENT DOCUMENTS 9,408,741 B2    8/2016  Blurton et al.
9,427,222 B2    8/2016  Galbierz et al.
(Continued)

FOREIGN PATENT DOCUMENTS

WO    WO-2017205212 A1 * 11/2017 ............. A61B 17/02

OTHER PUBLICATIONS

International Search Report for PCT/US2021/018837 mailed May 6, 2021.
(Continued)

*Primary Examiner* — Julianna N Harvey
(74) *Attorney, Agent, or Firm* — Sandberg & von Gontard P.C.

(57) ABSTRACT

An adhesive convertible tissue stabilizer is provided which can be applied preoperatively to a patient to retract tissue to facilitate a medical/surgical procedure. As a perioperative device, the convertible device accepts most, if not all, surgical preparations, enabling the creation of a sterile field. At the completion of the procedure, the convertible device is converted from a perioperative device to a post-operative device by removal of a layer of the convertible device.

21 Claims, 8 Drawing Sheets

(51) Int. Cl.
    *A61F 13/05*   (2024.01)
    *A61M 1/00*    (2006.01)
(52) U.S. Cl.
    CPC ..... *A61M 1/912* (2021.05); *A61B 2017/0212* (2013.01); *A61M 2205/0216* (2013.01)

(56) References Cited

U.S. PATENT DOCUMENTS

| | | |
|---|---|---|
| 9,439,808 B2 | 9/2016 | Woodroof et al. |
| 10,653,404 B2 | 5/2020 | Galbierz et al. |
| 2016/0007980 A1 | 1/2016 | Galbierz et al. |
| 2016/0338687 A1 | 11/2016 | Blurton et al. |
| 2017/0119586 A1 | 5/2017 | Hansen |
| 2018/0008477 A1 | 1/2018 | Galbierz et al. |
| 2018/0010025 A1* | 1/2018 | Hartwell ................ C09J 201/02 |
| 2018/0110659 A1* | 4/2018 | Galbierz ............. A61F 13/0236 |
| 2019/0159768 A1* | 5/2019 | Galbierz .................. A61F 5/37 |

OTHER PUBLICATIONS

Written Opinion for PCT/US2021/018837 mailed May 6, 2021.
International Preliminary Report on Patentability for PCT/US2021/018837 mailed Mar. 14, 2022.

* cited by examiner

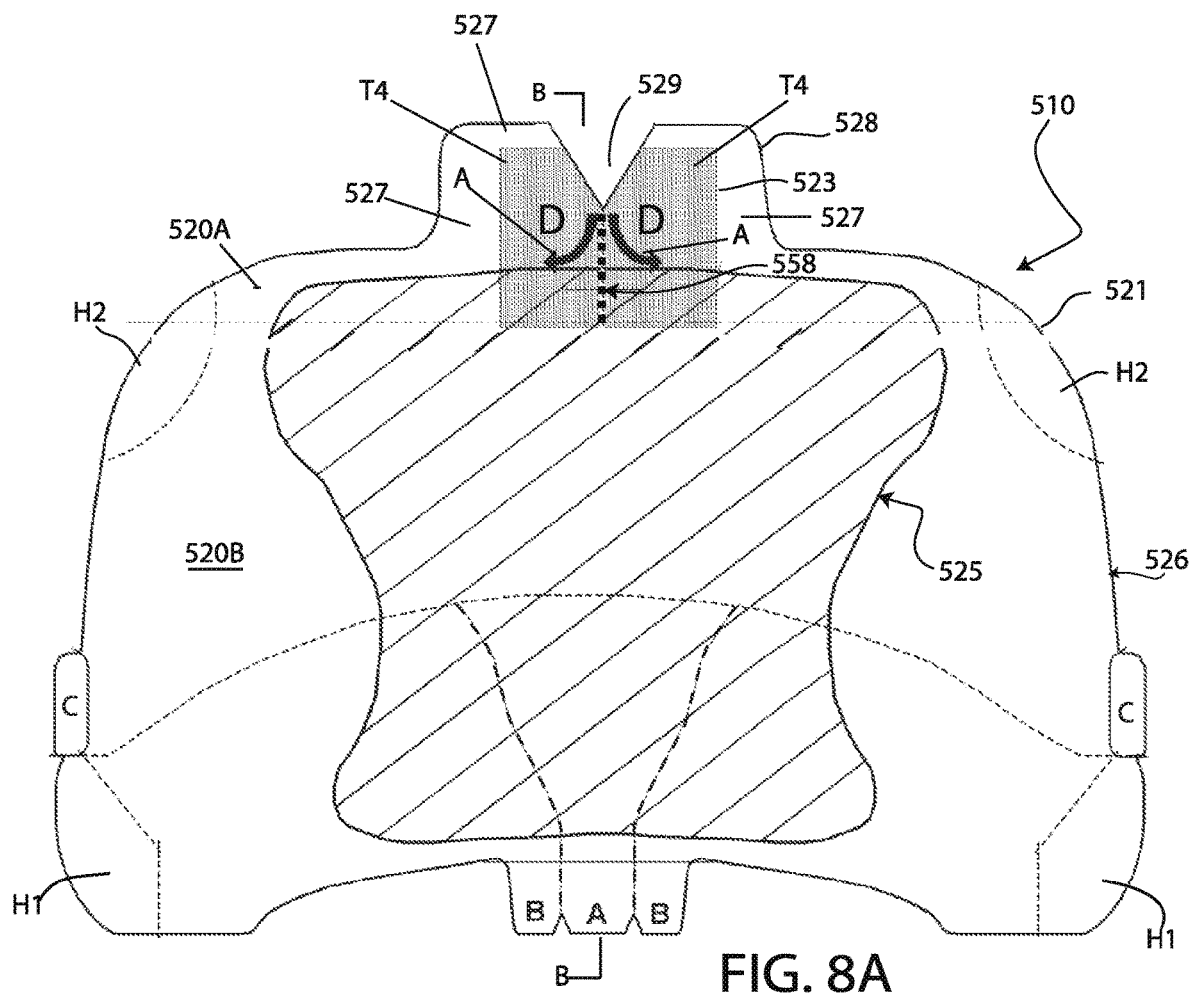
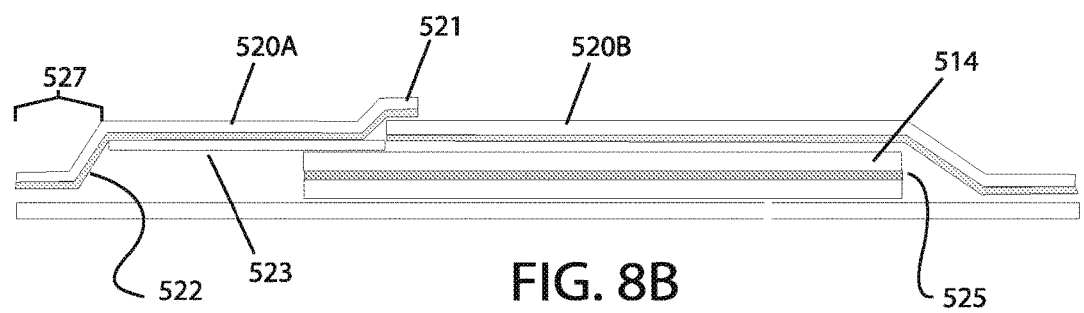

CONVERTIBLE TISSUE RETRACTOR

CROSS-REFERENCE TO RELATED APPLICATIONS

This application is the US National Stage under 35 USC §371 of International Application No. PCT/US2021/018837, filed 19 Feb. 2021 which claims priority to U.S. App. No. 62/981,377 filed 25 Feb. 2020 and entitled "Convertible Tissue Retractor/Wound Cover." The content of said applications (including drawings and claims) is incorporated herein by reference.

STATEMENT REGARDING FEDERALLY SPONSORED RESEARCH OR DEVELOPMENT

Not Applicable.

BACKGROUND

This application relates to a surgical device which in one aspect can be used to retract and retain excessive or redundant tissue in a retracted position during a surgical or medical procedure and in a second aspect can facilitate post-procedure healing of surgical wounds.

In our U.S. Pat. Nos. 9,427,222 and 10,653,404 we disclose devices which can retract and stabilize excessive and/or redundant tissue during a surgical or medical procedure; and in our Pub Nos. US 20180008477 and US 20190159768 we disclose retractors which can be worn for extended periods of time to retain excessive and/or redundant tissue in a retracted position to allow for healing of a wound that would otherwise be covered by the excessive and/or redundant tissue. All of the noted patents and published applications are incorporated herein by reference.

The disclosed devices work well for their intended purpose, and, in particular, the commercial device manufactured under U.S. Pat. No. 9,427,222 has been received with acclaim. However, it is not designed to convert from perioperative to a post-operative device.

The overall design could also be modified so that the device can be converted from a device used during the procedure to a device worn post-procedure to facilitate wound healing.

BRIEF SUMMARY

An adhesive convertible tissue stabilizer is provided which can be applied preoperatively to a patient to retract tissue to facilitate a medical/surgical procedure. As a perioperative (or preoperative) device, the convertible device accepts most, if not all, surgical preparations, allowing for sterile surgical site to be achieved. At the completion of the procedure, the convertible device is converted from a perioperative device to a post-operative device by removal of a layer of the convertible device. Inasmuch as the post-operative portion is already adhered to the patient, as described below, this action does not affect the existing position or the fixation on the patient of the post-operative device upon removal.

In accordance with a first aspect, the convertible adhesive device comprises a perioperative portion having an upper surface and a lower surface, and comprising a top layer; the top layer preferably being fluid impermeable and having an elongation factor less than an elongation factor of the post-operative portion; a release liner; and a post-operative portion. The perioperative portion is removably adhered to the upper surface of the post-operative portion; and the release liner is removably adhered to the lower surface of at least the post-operative portion by means of an adherent.

Preferably, the post-operative portion comprises a fabric layer. The post-operative portion can, for example, be comprised of a tricot nylon knit fabric or a woven fabric. In a preferred embodiment, the post-operative portion is a nylon fabric.

The adherent can comprise a silicone gel, an acrylate adhesive, or both. In a preferred embodiment, the adherent comprises the silicone gel. Preferably, the adherent covers substantially the entire bottom surface of the post-operative portion.

In accordance with an aspect of the convertible adhesive device, the lower surface of the top layer is substantially covered with an adhesive (separate from the adherent) to removably secure the top layer to at least the upper surface of the post-operative portion. Preferably, this adhesive if is an acrylate adhesive or coadhesive.

In accordance with an aspect of the convertible adhesive device, an elongation factor of the perioperative portion is not greater than an elongation factor of the post-operative portion, such that the perioperative portion arrests the elongation of the post-operative portion when the convertible device is initially applied to a patient.

In accordance with an aspect of the convertible adhesive device, the post-operative portion and the perioperative portion are co-extensive with each other, and the release liner is co-extensive with the post-operative portion. In a variation, the post-operative portion can be provided with a through-cut defining a periphery of a central portion of the post-operative portion, whereby a margin is formed between the periphery of the central portion and edges of the post-operative portion. This variation allows for the practitioner to effectively select between two sizes of post-operative portions—a large post-operative portion which is the same size as the perioperative portion, or a post-operative portion which is smaller than the perioperative portion.

In accordance with an aspect of the convertible adhesive device, the perioperative portion is larger in extent than the post-operative portion, such that the perioperative portion defines a margin between edges of the post-operative portion and edges of the perioperative portion. In this aspect, the perioperative portion has a lower surface having an adhesive thereon, and the release liner is removably adhered to the top layer in the margin, and the margin is adapted to be adhered to a patient during use. In particular, the adhesive is applied to the lower surface of the top layer in the margin.

In accordance with an aspect of the convertible adhesive device, the adhesive covers substantially the entire lower surface of the perioperative portion (i.e., of the top layer).

In accordance with an aspect of the convertible adhesive device, the top layer can comprise a first portion and a second portion separate from the first portion; whereby the first portion overlaps the second portion, at least in part. In this aspect, the first portion comprises a tab at an edge of the overlapping portion to facilitate removal of the top layer from the device.

The overlap between the first and second portions of the top layer can extend horizontally (i.e., from side-to-side) or vertically (i.e., from top-to-bottom) of the convertible adhesive device.

In a variation the tab comprises a flap extending from an edge of the first portion over the second portion.

In another variation, wherein the convertible adhesive device includes a piece of material adhered to the lower surface of the perioperative portion and having a bottom surface free of adhesive. This piece of material can extend, for example, from a top edge of the perioperative portion to a point over the post-operative portion, and can have a width substantially less than a side-to-side width of the post-operative portion. This piece of material thus enables the overlap to define a tab (by defining a region of the top portion that is not adhered to the lower portion, to facilitate removal of the perioperative portion from the post-operative portion.

In a variation, the convertible adhesive device can include a notch extending inwardly from the top edge of the perioperative portion; the piece of material extending to the top edge of the perioperative portion in the notch. The convertible adhesive device can include a perforated cut line extending from a bottom of the notch to a bottom edge of the piece of material. This perforated cut line would extend through the perioperative portion and the piece of material, but not through the post-operative portion.

In accordance with an aspect of the convertible adhesive device, a perforated line can be formed in the perioperative portion over the post-operative portion. In this aspect, the convertible adhesive device includes at least one tab having a secured portion adhered to the top surface of the top layer on a first side of the perforated line and a grasping portion; the adhered portion having a first end proximate the perforated line and a distal end remote from the perforated line. In this aspect, the grasping portion of this tab extends from the proximate end of the adhered portion.

In a variation, the tab is a first tab, and the convertible adhesive device includes at least one second tab; the second tab having a secured portion adhered to the top surface of the top layer on a second side of the perforated line and a grasping portion. The adhered portion has a first end proximate the perforated line and a distal end remote from the perforated line. The grasping portion of the tab extends from the proximate end of the adhered portion; whereby the second tab is oriented in a direction opposite the first tab.

In a variation, the perforated line is generally bell-shaped.

In a variation, the convertible adhesive device includes a second perforated line extending through a cross-portion of the bell-shaped perforated line.

In accordance with an aspect of the convertible adhesive device, the convertible adhesive device includes means for monitoring physiological conditions of a patient. The monitoring means comprises a sensor array and a receiving device which receives information from the sensor array representative of the physiological condition being monitored. The sensor array can be positioned on the device to be in sensing relationship with the patient when the device is applied to a patient. The sensor array can include either a transmitter to transmit the information or a readable storage medium to store the information. In the former case, the receiving device comprises a smart phone, tablet, computer, or the like running appropriate applications (apps); and in the latter case, the receiving device comprises a reader which can read the information stored on the storage medium.

The sensor array can be adapted to monitor one or more of temperature, humidity, pH of the patient's skin, static/charge of the device and/or skin, motion, stress (i.e., physiological effects) to the patient's skin, tension/stretching of the device or a layer or portion thereof, blood oxidation, heart rate, etc.

In a variation, the parameters being monitored are thermal and/or photo spectroscopic indicating.

In a variation, the monitoring means comprises an alarm which is activated in response to a monitored condition being outside of a predetermined range; the alarm being selected from the group consisting of an auditory alarm, a visual alarm, a tactile alarm, and combinations thereof. In this variation, the receiving device can include the alarm.

In accordance with an aspect of the convertible adhesive device, the convertible adhesive device can include at least (1) one port and/or (2) a port assembly and flanged cannula positioned in the post-operative portion.

The port assembly comprises a tube passing through the post-operative portion, and the tube is adapted to be connected to a vacuum or pressure source.

In a variation, the convertible adhesive device includes a wound dressing below the hollow tube; the wound dressing being positioned to be between the patient and the tube when the device is applied to a patient.

In accordance with an aspect of the convertible adhesive device, the device is anchored on the patient, typically or preferably at a supra pubic area of the patient, so that tension is evenly applied to tissue, Preferably, the device is applied to tissue horizontally across the patient to extend over the patient's iliac crests (i.e., from iliac crest to iliac crest). The device is maneuvered in a consistently smooth and uninterrupted motion generally in a cephalad direction, and attached at or near a xiphoid area of the patient.

In accordance with an aspect of the convertible adhesive device, wherein the convertible adhesive device is a multi-ply device and the layers or plies thereof are comprised of a combination of materials formulated from monomers polymers and co-polymers to construct the desired layers.

In a variation, the silicone gel of the tissue stabilizing cover may be a coadhesive silicone gel.

In accordance with an aspect, a method is disclosed for converting a convertible adhesive device according to any of the aspects or variations described above from a perioperative panniculus retractor that was applied aseptically to a patient prior to a medical/surgical procedure to a post-operative panniculus retractor. The method comprises removing the perioperative portion from the post-operative portion after the convertible adhesive device has been applied to a patient (and preferably after a surgical/medical procedure has been completed).

In accordance with an aspect of the method, the post-operative portion can be removed from, cleaned and/or sterilized, and reapplied to, the patient.

In accordance with an aspect of the method, the post-operative portion can be worn by the patient for at least ten days.

In accordance with an aspect, the use of a convertible adhesive device, as described above is disclosed.

In accordance with an aspect of the use of the convertible adhesive device, the post-operative device portion can be used independently of the perioperative portion.

In accordance with an aspect of the use of the convertible device, after removal of the perioperative portion, loading occurs in the post-operative device, and the post-operative portion can be adjusted and loaded to accommodate the need of the patient/clinician.

BRIEF DESCRIPTION OF THE DRAWINGS

FIG. 8A is a plan view of another alternative embodiment of the convertible device in which the top layer is formed from two pieces; and FIG. 8B is a cross-sectional view of the convertible device of FIG. 8A taken along line 8B-8B.

Corresponding reference numerals will be used throughout the several figures of the drawings.

DETAILED DESCRIPTION

Figure 1:
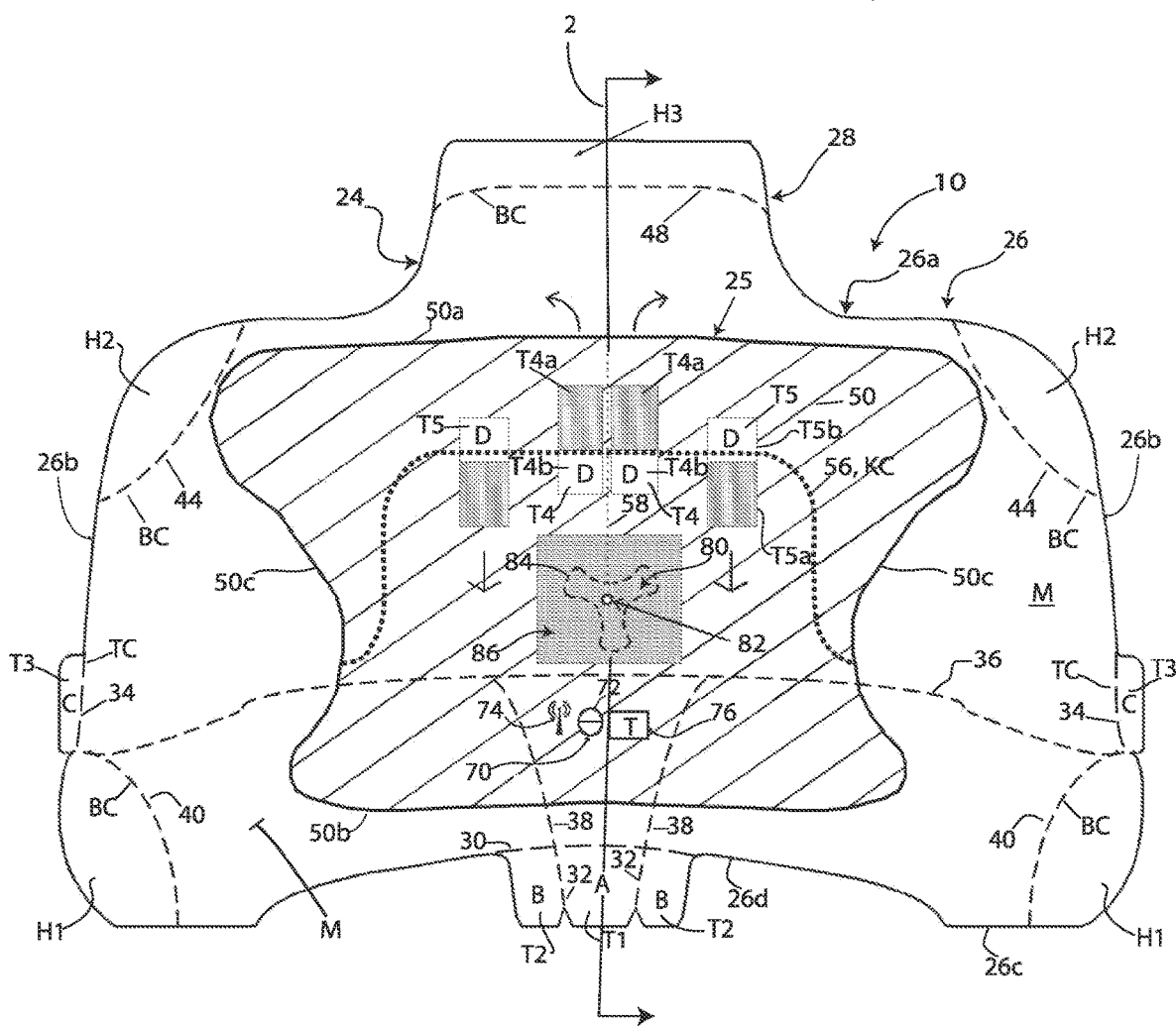
FIG. 1 is a plan view of a convertible device.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Broadly speaking, a convertible device 10 (shown generally in FIG. 1) is two devices in one. Initially, the convertible device 10 is applied preoperatively and is used to retain excess/redundant tissue or flesh (such as a panniculus) in a retracted position to facilitate access to a site (such as an abdominal site) during of a medical or surgical procedure. The device 10 is a multi-ply sheet panniculus retractor, which in an illustrative embodiment, is anchored distally to the supra pubic area or lower abdomen of the patient. Preferably, the device is applied in a manner such that tension is evenly applied to tissue horizontally across the patient such that it extends over the patient's iliac crests (i.e., from iliac crest to iliac crest). The device is used to lift or shift excessive and/or redundant tissue in a single motion, typically in a cephalad direction. For example, a top or proximal portion of the convertible device can be elevated, preferably at a 30-degree elevation, and moved in a consistently smooth and uninterrupted motion until the redundant tissue is retracted. The convertible device is then anchored proximally at or around the diaphragm. The resulting retraction is accomplished with a multi-ply single sheet retractor anchored at lower and upper areas on the patient with a bottom surface substantially completely covered with adhesive.

As a perioperative device, the device 10 will retain the redundant tissue away from the surgical/medical site during the medical/surgical procedure to fully expose the surgical site. As a perioperative device, the convertible device accepts all surgical preparations, allowing for a sterile surgical site to be achieved. At the completion of the procedure, the convertible device is converted from a perioperative device to a post-operative device by removal of a layer of the convertible device, as will be described below. As can be appreciated, the post-operative device is applied to the patient along with the perioperative device. Further, the adhesive adhering the perioperative device to the post-operative device is weaker than the adhesive adhering the post-operative device to the patient. Thus, the action of removing the perioperative device does not disturb the post-operative device, and the post-operative device will remain applied to the patient in its existing position. That is, the position of the post-operative device does not change during removal of the perioperative device. The post-operative portion can be worn by the patient, post-operatively, for 10-14 days, and can be removed and reapplied. During this healing period, the post-operative portion will lift, hold, suspend and secure excessive and redundant tissues away from the incisional site for extended periods of time.

If the post-operative portion is removed for repositioning on the patient, the post-operative portion can be washed with mild soap and water prior to reapplication to the patient.

When the convertible device 10 is applied to a patient, the sheer forces applied by the retracted excess tissue that accompany the lifting motion are transferred to the device. The device utilizes fabric, typically nylon with stretchable fibers, such as Lycra®, with a thick coat-weight copolymer to absorb the sheer forces by accumulating the sheer in a gel (such as a silicone gel) and transfers the energy to the nylon. If the sheer forces accumulated in the gel exceed the designed limitations, the device will release or peel from the epidermis before injury can occur, limiting the sheer forces applied to the skin of the patient. If the post-operative portion is removed, the adhesive (i.e., silicone gel and/or acrylate) will stay with the fabric layer of the post-operative portion so that the post-operative portion can be reapplied.

Referring to the figures, a convertible device 10 of the present invention comprises a release layer 12, which can, for example, be made from LDPE, HDPE and the like, and may be coated with fluorosilicone or other coatings which reduce the pull forces required to release the liner from the silicone and does not affect the acrylate adhesive. Any other desired material can be used for the release layer 12. A fabric layer 14 is removably adhered to the release liner 12 by an adherent 15. The adherent 15 can comprise a binder 16 and a silicone gel 18. In this instance, the binder 16 adheres the silicone gel 18 to the fabric layer 14, and the silicone gel is adjacent the release liner 12. As is known, silicone gels are typically composed of a very lightly cross-linked silicone elastomer whose polymer network has been swollen with silicone fluids. Additionally, the binder 16 can be an acrylate adhesive, such that the acrylate adhesive binder will adhere the silicone gel to the fabric layer 14. The adherent extends substantially over the entire lower surface of the fabric layer 14. As seen, the release liner 12 does not directly contact the fabric layer 14. Thus, the release layer is removably adhered to the bottom of the fabric layer by the adherent 15. The fabric layer 14 can, for example be made from a woven nylon, such as is described in U.S. Pat. No. 9,439,808B2. Alternatively, the fabric layer can be made from a warp knit fabric, such as a tricot knit fabric, preferably of nylon.

A top layer 20 (also referred to as a carrier liner) covers the fabric layer 14, and is removably adhered to the fabric layer 14 by means of a weak adhesive 22, such as a pressure sensitive acrylate adhesive. The adhesive 22 covers substantially the entire lower surface of the top layer 20. This top layer 20 can be made from a polyethylene, and is preferably gas and liquid impermeable.

For purposes of manufacturing the convertible device 10, the fabric layer 14 and adherent 15 (such as, the binder 16 and the silicone gel 18) can be provided as a sheet assembly which is then combined with the release layer 12 and the top layer 20. A commercially available version of such a sheet assembly is sold by Polymer Science, Inc., under the product name P-Derm® PS-1255 or PS-1480. Alternatively, this sheet assembly can be formed, for example, as disclosed in U.S. Pat. No. 9,439,808 which is incorporated herein by reference and which discloses a wound dressing comprised of silicone membrane layer and a woven nylon fabric layer. The fabric layer 14 with the adherent 15 and the top layer 20 are both more pliable than the release layer 12. Thus, in production, a single multi-ply sheet from which the device is made is formed by positioning the fabric layer 14 with the adherent 15 on the release liner, and then placing the top layer 20 over both fabric layer 14 and the release liner 12. The convertible device can then be die cut from the sheet so formed.

The top layer 20 defines the perioperative portion 24 of the convertible device 10, and the fabric layer 14 defines the post-operative portion 25 of the convertible device 10. As will become apparent below, the post-operative portion 25 is generally applied to the patient with the perioperative portion. In the device as illustratively shown in FIG. 1, the perioperative portion is larger than the post-operative portion, and there is a margin M between the perimeter of the post-operative portion 25 and the perioperative portion 24 which fully covers the post-operative portion 25. The area defined by the post-operative portion 25 can be 50% of the area of the perioperative portion. Preferably, the post-operative portion 25 is positioned relative to the perioperative portion 24 such that there is a margin surrounding the post-operative portion 25. However, as discussed in conjunction with FIG. 4, below, the convertible device 10 can be provided with the post-operative portion (i.e., the cloth layer) and the perioperative portion (i.e., the top layer) being generally co-extensive and of generally equal size. In this latter instance, there would be no margin surrounding the post-operative portion 25. Further, the post-operative portion can define an area between 50% and 100% of the area of the perioperative portion. Thus, the post-operative portion can be 50%, 55%, 60%, 65%, 70%, 75%, 80%, 90%, or 95% of the area of the perioperative portion. Generally, it is desirable that the post-operative portion be generally centered relative to a body area of the perioperative portion.

Figure 2:
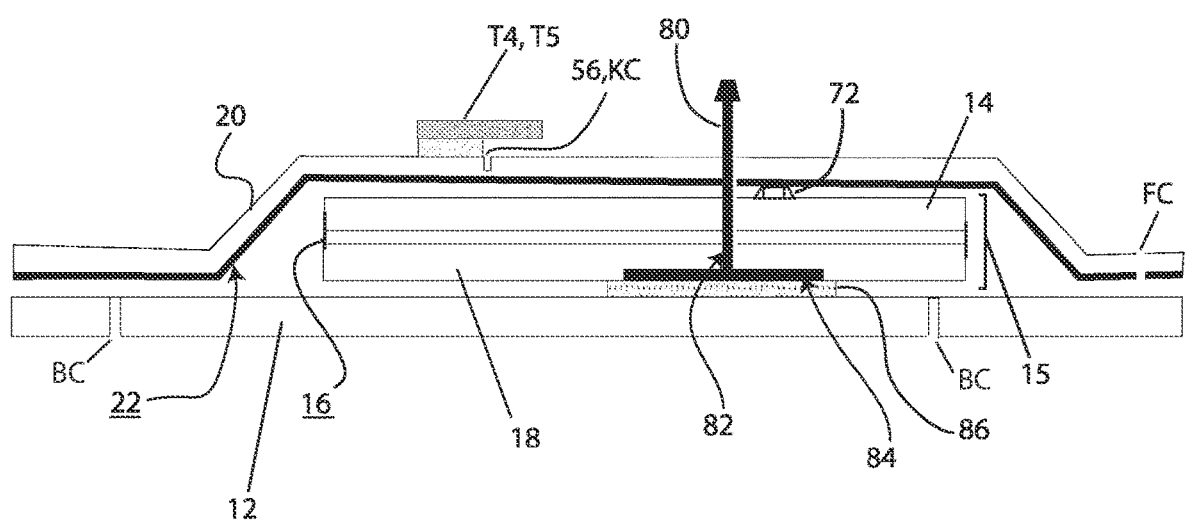
FIG. 2 is a schematic cross-sectional view of the device taken along line 2-2 of FIG. 1.

The convertible device 10 is typically provided with, and is illustratively shown as having, a plurality of tabs (T1-T3) and hand holds (H1-H3) which are defined by back cuts (BC) and top of face cuts (FC) in the top layer 20 (FIG. 2) which facilitate handling of the device when positioning the device on, and adhering the device to, the patient. After adhering the device to the patient, the top layer 20 also allows for the convertible device to be prepped (or sterilized). Thus, sterilization of the preoperative portion simultaneously preps (or sterilizes) the post-operative portion.

To enable use of the convertible device 10, a series of cuts are formed in the top layer 20 and release liner 12 to facilitate removal of the release liner 12 from both the top layer 20 and the fabric layer 14. Some cuts are top or face cuts which extend just through the top layer (but not through the release liner 12 or fabric layer 14), and other cuts are back cuts which extend just through the release liner 12, but not through the top layer 20 or fabric layer 14. Back cuts are used to form integral protected grasping areas H1-H3 at "corners" and top of the device. The back cuts which form or define the grasping areas allow for the release liner 12 to remain with the top layer in these areas. This allows for medical personnel to hold and position the device when a portion, or all, of the release liner 12 (except for the release liner in the protected grasping areas) has been removed from the top layers without having their gloves contact the adhesive of the top layers. Back cuts can also be formed to divide the release liner into discrete sections or panels which can be removed independently of each other. Additionally, the device can include kiss-cuts KC in the top layer 20 which facilitate conversion of the device from a perioperative device to a post-operative device.

To facilitate removal of the release liner, each panel of the release liner can be provided with at least one tab. The tab enables the technician to remove the release liner from the top layers (i.e., the fabric layer 14 and top layer 20) of the device without coming into contact with the adhesive of the top layers. In an illustrative embodiment, the tabs are formed from the sheet from which the top layer 20 is formed. That is, the tabs are integral with the body of the device. To this end, the tabs can be defined by top slices or top cuts at an upper or inner end of each tab. These top cuts cause the top layer 20 to remain with the release liner 12 in the area of the tab. Thus, the medical personnel can simply grasp a tab and pull downwardly (away from the top layer) to separate the release liner 12 (or portion of the release liner) from the top layers. These tabs allow for the practitioner to remove the release liner without his or her gloves contacting the adhesive of the top layer or the fabric layer. In another embodiment of the tabs, the tabs are formed separately from the device body (i.e., is not integral with the device) and are adhered to the release liner of the device.

The various slices or cuts are generally through cuts. That is, the back cuts extend through the release liner (but not through the top layer or fabric layer) and the top cuts extend through the top layer (but not through the release liner or fabric layer). Full cuts, which extend through both the top layer and the release liner, and kiss cuts, which extend only partially through a specified layer, are noted in certain circumstances. Thus, there is no weeding, folding, bending or crack back needed to operate the tabs and/or remove the release liner.

Turning to FIG. 1, a convertible device 10 has a generally quadrilaterally shaped body 26 having an upper edge 26a, side edges 26b, and a lower edge 26c. The lower edge 26c is cut to define a concave arc section 26d. This curved shape is preferred because it typically better fits the patient's anatomy (i.e., the contour of the abdomen where the device is applied to a panniculus) when in use. Stated differently, the curved section 26d of the lower edge 26c defines a concave radius or curvature that simulates or represents the curvature of patient's abdomen. However, it will be appreciated that the lower edge could be generally straight or even convexly curved if desired. The device also includes a tongue or neck 28 extending generally from the center of the upper edge 26a. When corners of the convertible device are sharp (i.e., right angled), there is a tendency for the top layer to lift off the patient's skin due to the concentration of stresses and forces at the right-angle corner. Thus, the corners of the device 10 are shown to be radiused. However, the corners could be sharp corners, if desired. It will be appreciated that the body 26 of the device forms a body of the perioperative portion 24 of the device.

A first tab T1, labeled "A" in the drawings, extends from the center of the bottom curved edge 26d. Two tabs T2, labeled "B" in the drawings, are formed on opposite sides of the A-tab T1, and likewise extend from the bottom curved edge 26d. The B-tabs T2 are shown to be adjacent the A-tab T1, but could be spaced from the A-tab, anywhere along the bottom edge 26c,d of the device body portion 26. Side tabs T3, labeled "C" in the drawings, are formed above the bottom right and left corners of the device 10 and extend from the side edges 26b. However, as seen, the outer edges of the C-tabs T3 are essentially even or flush with the upper edge of the lower corners of the device. Although near the bottom of the device, the side C-tabs T3 could be formed at any desired point along the side edges 26b of the device body portion 26. As seen, the B-tabs T2 are adjacent the A-tab T1, and thus a single face cut 30 extends across a top of the three tabs. The A- and B-tabs are separated from each other by full cuts 32 which extend through both the top layer 20 and the release liner 12, so that the tabs are fully independent of each other. Top cuts 34 extend generally parallel to the side edges 26b of the device body 26 along an inner end of the side C-tabs T3. The tabs T1-T3 are all shown to be "outboard" tabs. That is, they extend from the respective edges of the body of the device. If desired, the tabs T1-T3 could be formed as "inboard" tabs, in which case, they would not protrude from the body of the device. Rather, their outer edges would be defined by the outer edges of the body. If "inboard" tabs are used, the cut lines 30 and 34 which define inner ends of the tabs could be more U-shaped.

A back cross-cut 36 extends from one side edge 26b to the other side edge 26b to divide the release liner 12 into an upper panel and a lower panel. This back cross-cut 36, like the curved section 26d of the lower edge 26c, defines a generally concave radius or curvature that simulates or represents the curvature of patient's abdomen. However, the back cross-cut 36 need not be parallel to the curved edge 26d of the device. As shown, the release liner lower panel comprises about the lower one-third of the body 26. Back cuts 38 extend upwardly from each corner of the A-tab 20 to the back cross-cut 36. The back cuts 38 divide the backing lower panel into a central alignment portion, which is used to orient and anchor the device on the patient, and side portions which encase the radius of the excessive and/or redundant tissue (e.g., the panniculus) and further anchors the device to the patient's dermis. The two back cuts 38, which define the lower panel central portion extend upwardly and outwardly, giving the central portion the shape, in general, of a funnel. As seen, the A-tab T1 is connected to the central portion and a B-tab T2 is connected to each of the side portions. This construction allows for the three sub-panels of the lower panel to be removed from the top layers independently of each other by means of their respective tabs, and allows for the practitioner to expose only a portion of the adhesive of the top layers, thereby making application of the device to a patient's skin somewhat easier.

Back cuts 40 are made inwardly of the lower corners of the body 26 in the lower panel to define lower grasping areas H1. Upper grasping areas H2 are defined by back cuts 44 at the upper corners of the upper panel. Lastly, a grasping area H3 is formed on the neck 28 by a back cut 48. The cuts 40, 44 and 48 enable the release liner 12 to remain with the top layer 20 in each of the grasping areas H1-H3. These grasping, or holding, areas form areas in which the adhesive remains covered during application of the device 10 which the medical practitioner can hold on to without fear of his/her gloves becoming stuck to the adhesive of either the cloth layer 14 or the upper layer 20.

Although the grasping areas H1-H3 are described as being defined by back cuts and thus as being integral with the device, they could be formed by separate grasps or handles which are adhered to the top layer. These grasping areas or handles would accomplish the same function as the grasping areas which are integral with the device—they would allow for the technician to hold the top layers of the device without contacting the adhesive of the top layers after the release liner has been removed.

The post-operative portion 25 (defined by the fabric layer 14), is smaller than the top layer 20, and has top, bottom, and side edges 50a-c. The upper and lower edges 50a,b are generally parallel to each other, and the side edges 50c are generally concave. The side edges 50c are joined to the top edges 50a and bottom edges 50b via radiused corners. The upper corners have a larger radius than the lower corners, and the top edge 50a is longer than the bottom edge 50b. Thus, the overall shape of the post-operative portion 25 may be that of an inverted trapezoid with concave side edges. This is similar to the shape of the device disclosed in our Pub. No. US2019-0159768 which is incorporated herein by reference.

A perforated line 56 is formed in only the top layer 20. As shown in FIG. 1, this perforated line 56 has opposite ends which "intersect" with, or end at, the side edges of the post-operative portion. Starting at the periphery 50c of the post-operative portion, the perforated line 56 turns upwardly near its ends, and then turns inwardly, to define an upside down U with outturned ends. A second perforated line 58, again formed only in the top layer 20, extends from the top edge 50a of the post-operative portion and extends downwardly to, and beyond, an upper horizontal portion of the perforated line 56. The perforated line 58 effectively bisects the perforated line 56, and defines generally a center line of the post-operative portion 25. The perforated lines 56 and 58 are preferably formed as kiss-cuts. Four tabs are adhered to the top layer 20 and cross the horizontal portion of the perforated line 56. There are two inner tabs T4 and two outer tabs T5, all labeled "D" in FIG. 1. The inner tabs T4 are located on opposite sides of perforated line 58 and have a secured portion T4a adhered to the top layer above the horizontal portion of the perforated line 56, and a grasping portion T4b below the horizontal portion of the perforated line 56. The outer tabs T5 are positioned outside of the inner tabs T4 and are positioned oppositely the inner tabs. That is, the outer tabs T5 have a secured portion T5a adhered to the top layer below the horizontal portion of the perforated line 56, and a grasping portion T5b above the horizontal portion of the perforated line 56. As seen in the FIG. 1, the grasping portions of tabs T4 and T5 can cross over the horizontal portion of the perforated line. As will be described below, when the tabs T4 and T5 are pulled, they will remove the top, polyethylene, layer 20 separating it from the fabric layer 14, to leave the fabric layer exposed.

Figure 3:
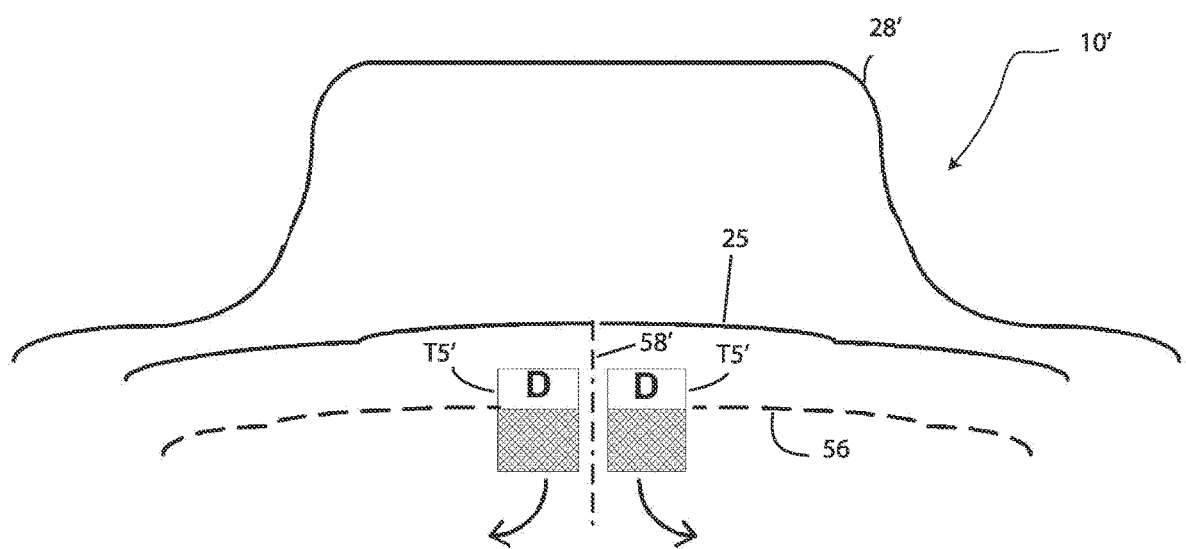
FIG. 3 is a fragmentary plan view of the convertible device of FIG. 1, but with only two tabs for removing the perioperative portion of the device from the post-operative portion of the device.

In an alternative configuration, the device 10 can be provided with only two tabs to remove the perioperative portion from the post-operative portion. In FIG. 3, the device 10' is shown with a pair of tabs T5' identical to the tabs T5, but which are positioned adjacent and on opposite sides of the perforated line 58'. Additionally, as seen, the perforated line 56 is moved upwardly, and is closer to the bottom of the neck 28'. The device 10' is otherwise identical to the device 10.

Application of the device 10, 10' to a patient is described in our prior U.S. Pat. No. 9,427,222, which is incorporated herein by reference. Briefly, the A tab T1 is initially pulled to remove the central portion section of the release liner lower panel. This exposes a relatively small portion of the adhesive 22 of the top layer 20 and the adherent 15 of the fabric layer 14 to facilitate positioning of the convertible device 10, 10' on the patient's panniculus (or other excess/redundant tissue). Once positioned, the two B tabs T2 are pulled to remove the right and left portions of the release liner lower panel to expose the adhesive 22 and adherent 15 in the lower portion of the device 10. The right and left sides of the lower portion of the device 10, 10' can then be adhered to the patient's panniculus. With the device positioned on the patient, the C tabs T3 can be pulled to remove the upper panel of the release liner from the top layer 20 and fabric layer 14. This will expose the adhesive 22 of the top layer and the adherent 15 of the fabric layer, except in the hand hold areas H2 and H3, where the release liner will remain in place. Grasping the device 10 at the hand holds H2 and H3, the practitioner will pull the device in a cephalad direction to pull the patient's panniculus headwardly relative to the patient, to displace the panniculus away from, and to better expose, the site for the medical/surgical procedure. When the panniculus is properly positioned, the neck portion 28 of the device is adhered to the patient. This is generally in the area of the patient's xiphoid process. The remainder of the device can then be adhered to the patient. Preferably, when the convertible devise is initially applied to the patient, the bottom or distal portion of the convertible device is anchored at a supra pubic area of the patient with tension being evenly applied to patient's tissue horizontally over the patient's iliac crests (i.e., from iliac crest to iliac crest). To retract the tissue, the top or proximal portion of the convertible adhesive device is then elevated, preferably at a 30-degree elevation, and by pulling on the device in a preferably consistently smooth and uninterrupted motion, the tissue is retracted until the top or proximal portion of the convertible device can be anchored generally at or near a xiphoid area of the patient. As can be appreciated, when the release liner 12 is removed, the adherent 15 will remain with the fabric layer 14.

The perioperative device 24 substantially spans the patient's panniculus from left to right. Thus, when the device is initially positioned on the patient, the device will be adhered to the panniculus along a large portion of the length of the patient's panniculus, spanning the patients iliac crests, as noted above. This allows for easier retraction of the panniculus as a whole as compared to multi-part devices, such as disclosed in Blurton, U.S Pat. No. 940874, which are adhered to only a small portion of the panniculus.

As can be appreciated, at this point, both the perioperative portion and post-operative portion of the convertible device 10 are adhered to the patient, with the post-operative portion being covered by the perioperative portion. Because the post-operative device 25 is smaller than the top layer 20/perioperative portion 24, the top layer 20/perioperative portion 24 will be adhered to the patient's skin only in the margin M of the top layer. The remainder of the top layer 20/perioperative potion 24 will be adhered to the fabric layer 14, which in turn is adhered to the patient via the adherent 15. The medical/surgical site can now be prepared, and the medical/surgical procedure can be carried out.

Once the medical/surgical procedure is complete, the perioperative portion (i.e., the top layer 20) can be removed from the patient to leave only the post-operative portion 25 (i.e., the fabric layer 14) of the device adhered to the patient. As noted above, this is accomplished by pulling the tabs T4 (if present) and T5. When the tabs T4 and T5 are pulled, they will remove the polyethylene top layer 20 from the fabric layer 14, to leave the fabric layer exposed. As noted above, the tabs T4 and T5 face in opposite directions. When the tabs T4 are pulled, they will remove the portion of the top layer between the perforated line 56 and the bottom edge 26c,d of the top layer; and when the tabs T5 are pulled, they will remove the portion of the top layer 20 above the perforated line 56. Further, the two sets of tabs are located on opposite sides of the perforated line 58. Thus, the two tabs T4 will remove right and left sides of the lower portion of the top layer, and the two tabs T5 will remove right and left sides of the upper portion of the top layer. Thus, the top layer 20 will tear along the perforated lines 56 and 58 as the top is being removed.

The hold of the adhesive 22 to the fabric layer 14 is weaker than the hold of the adherent 15 to the patient's skin. Thus, removing the top layer 20 will not remove the fabric layer 14 from the patient, and the fabric layer will stay in place on the patient. As seen, the tabs T4 and T5 are not at the edges of the post-operative portion 25, but rather, are positioned within the edges. Thus, when the tabs T4 and T5 are pulled, the tabs T4, T5 will not pull or tug at the edges of the post-operative portion 25, and therefore, the pulling of the tabs T4 and T5 is less likely to cause the post-operative portion to lift off the patient.

Figure 4:
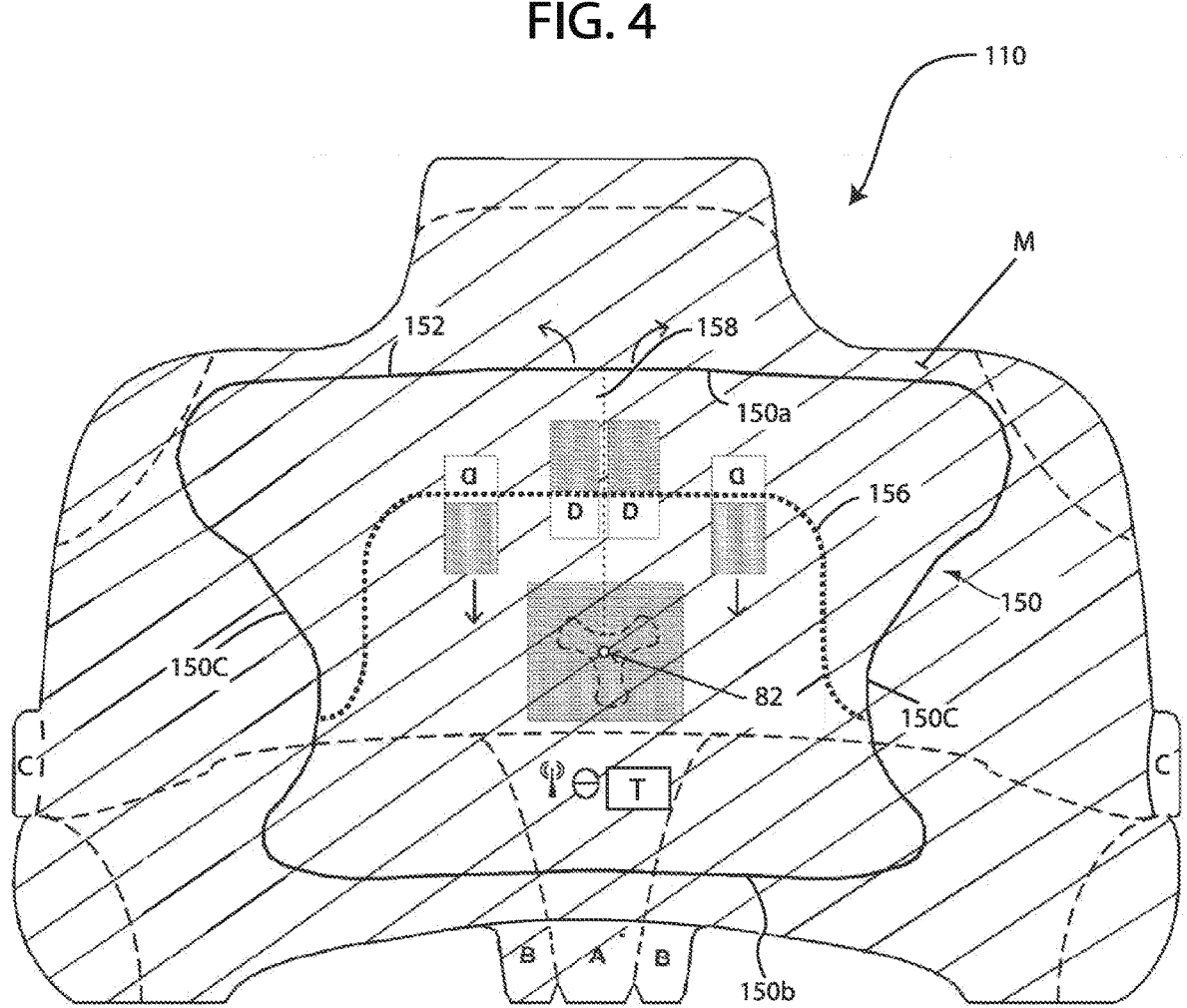
FIG. 4 is a plan view of an alternative embodiment of the convertible device.

An alternative embodiment of the device is shown in FIG. 4. In the device 110 of FIG. 4, the fabric layer 14 and top layer 20 are co-extensive with each other. Except as noted, the device 110 is generally identical to the device 10. The fabric layer 14 defines a central portion 150 defined by a, preferably continuous, cut 152 which defines top, bottom, and side edges 150a-c of the central portion. The central portion 150 is preferably the same size and shape as the post-operative portion 25 of the device 10. To facilitate removal of the top (polyethylene) layer from the fabric layer, the device 110 has a generally bell-shaped perforated cut 156 comprised of a pair of legs extending upwardly from below the bottom edge 150b of the central portion 150 to a point below the top edge 150a of the central portion which are joined by a horizontal portion which is generally parallel to 9 and below) the top edge 150a of the central portion. The perforated line 156 is generally identical to the perforated line 56, and thus, starting at the periphery 150c of the post-operative portion, the perforated line turns upwardly at the bottom of the legs, and then turns inwardly at the top of the legs, to define an upside down U with outturned ends. As with the device 10, in the device 110, the perforated lines 156 and 158 are preferably formed as kiss-cuts.

With the device 110, the cut 152 allows the practitioner to determine how much of the fabric layer will remain on the patient when the top layer is removed. The full fabric layer can remain on the patient if desired. Alternatively, as the polyethylene layer is removed, the portion M of the fabric layer surrounding the central portion 150 may be removed from the patient, leaving only the central portion 150 on the patient. This leaves a smaller post-operative portion of the device that can be worn by the patient long term (i.e., for several days, or even several weeks) to facilitate healing of an incision, wound, etc. as discussed in our Application Pub Nos. US2018-0008477 and US2019-0159768, which are incorporated herein by reference.

Figure 5:
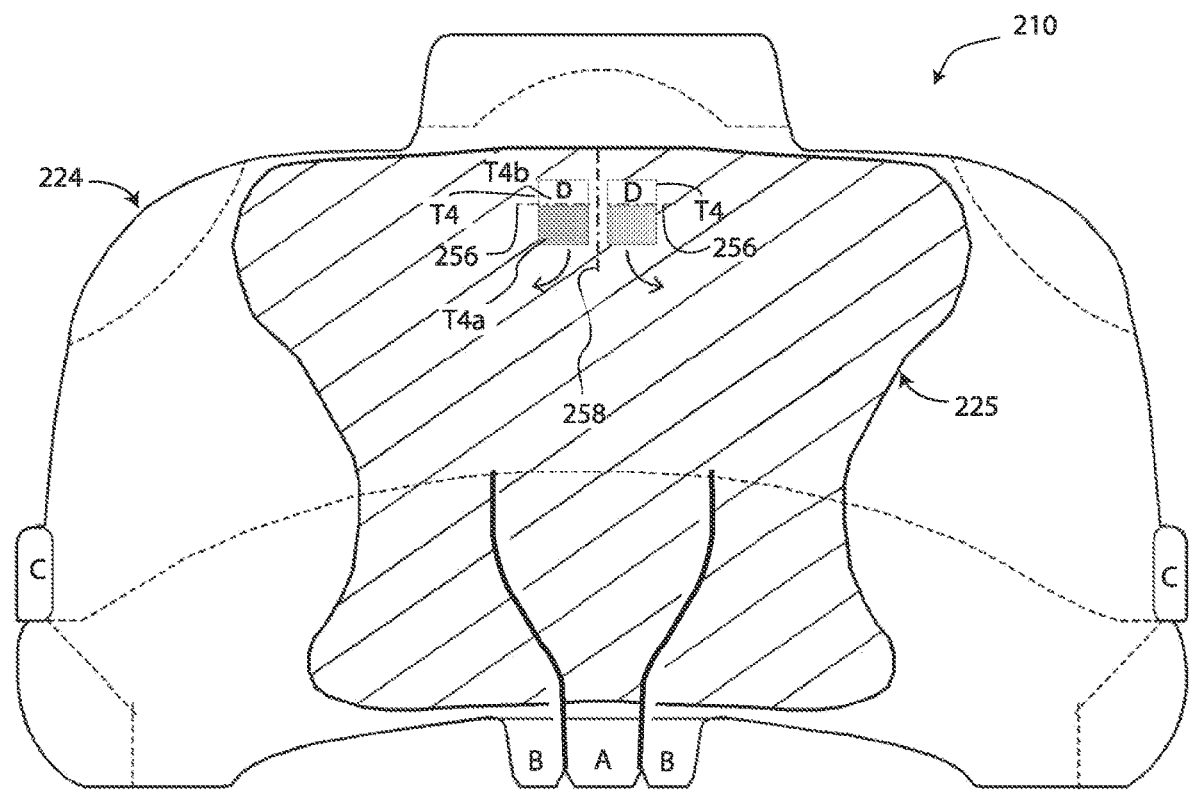
FIGS. 5 and 6 are plan views of a further alternative embodiment of the convertible device.
Figure 6:
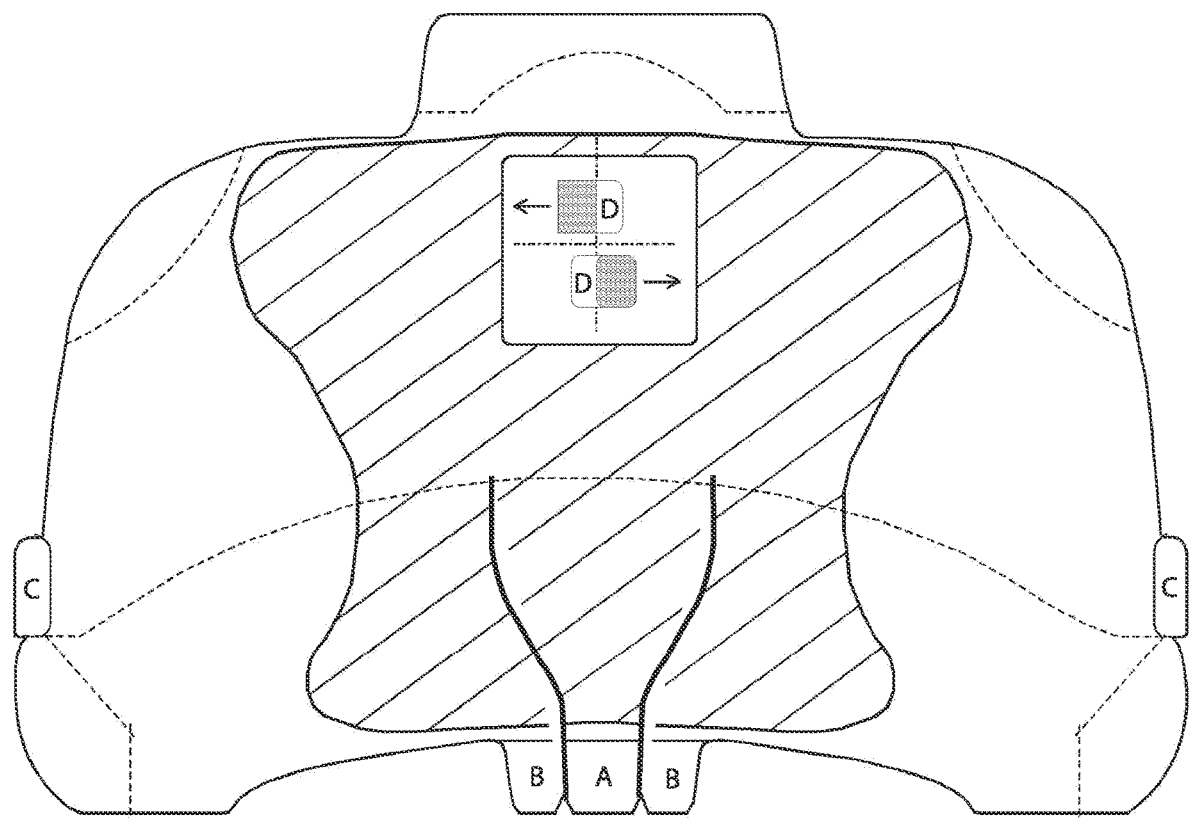

A further alternative configuration of the convertible device 210 is shown in FIG. 5. The convertible device 210 is similar to the device 10, in that the post-operative portion 225 defines an area smaller than the perioperative portion 224. However, as seen, the post-operative portion 225 is somewhat larger than the post-operative portion 25 of the device 10, in that it covers a larger portion of the top-to-bottom distance of the perioperative device 224. The primary difference between the devices 10 and 210 is that the device 210 includes only two D-tabs T4 positioned on opposite sides of a perforated line 258 in the top layer (perioperative device) and which extends from the top of the post-operative device to a point below the tabs T4. In this respect, the device 210 is similar to the device 10' of FIG. 3. Perforated lines 256 extend perpendicularly to the perforated line 258 and are positioned at the junction between the secured portion T4a and the grasping portion T4b of the tabs T4. As can be appreciated, by pulling on the tabs T4, the top layer (i.e., the perioperative portion) will be removed from the post-operative portion of the device. As shown in FIG. 6, the tabs T4 and the perforated lines 256 and 258 could all be rotated 90°, and the two tabs could face opposite directions. This configuration is advantageous in that it comports more readily to the positioning of personnel during a surgical procedure. Typically the personnel will be to the side of the patient.

Figure 7A:
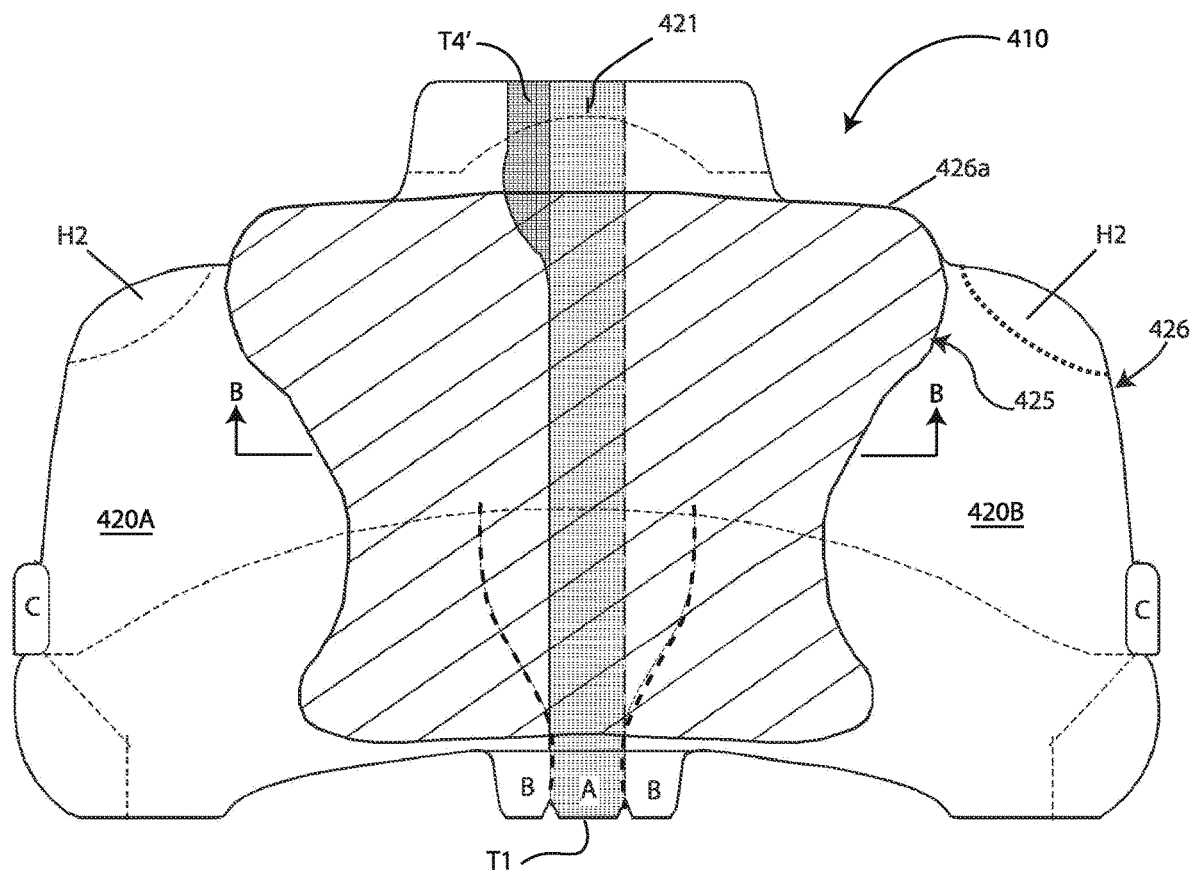
FIG. 7A is a plan view of another alternative embodiment of the convertible device in which the top layer is formed from two pieces.
Figure 7B:
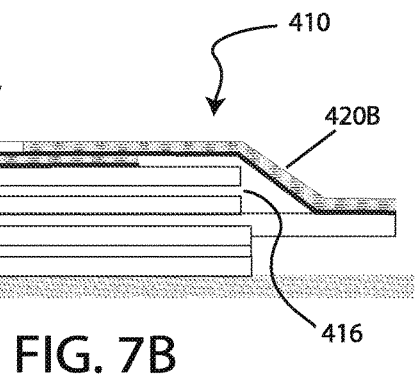
FIG. 7B is a cross-sectional view of the convertible device of FIG. 7A taken along line B-B of FIG. 7A.

FIGS. 7A-B shows a convertible device 410 which is based on the design of the convertible devices 10 (FIG. 1) and 210 (FIG. 5). The convertible device 410 differs from prior described devices in that the top layer is formed from two sheets 420A and 420B of film. The sheets 420A,B are made from the same material as the top layer 20 of the device 10. As shown diagrammatically in FIG. 7B, top layer 420B overlaps top layer 420A along an overlap area which, as seen in FIG. 7A, includes, and extends up from, the A-tab T1 at the base of the device 410. In the area 421 of overlap (shown as light grey in FIG. 7A), the lower surface of the top layer 420B may, or may not, have adhesive applied along the bottom thereof. A tab T4' extends from the edge of the top layer 420B to extend further over the layer 420A. As can be appreciated, pulling the tab T4' to right (with reference to FIG. 7A) will remove the top layer 420B to expose the layer 416 post-operative portion 425 comprised of a fabric layer 414 adhered to a silicone gel layer 418 by a binder 416

In addition, as seen in FIG. 7A, the post-operative portion 425 is larger than the post-operative portions 25 or 225. The post-operative portion 425 is shown to extend from just above the bottom edge of the perioperative portion (i.e., top layer) to the top edge of the perioperative portion. Further, as seen, the top edge 426a bumps upwardly, to be above the hand-hold areas H2 and the top corners of the body 426.

A further variation is shown in FIGS. 8A-B. The device 510 comprises a body 526 (forming the top layer/perioperative portion) and a post-operative portion 525. The top layer 520 is generally identical in shape to the top layer of the devices 10 and 210. However, the neck 528 has a V-shaped notch 529 formed in its upper edge, the function of which is described below.

Like the device 410, the top layer 520 is formed from two pieces, a top piece 520A and bottom piece 520B, which overlap along an overlap zone 521. However, the overlap zone 521 extends between the side edges of the body 526, rather than between the top and bottom edges. As seen in FIG. 8A, the overlap zone 521 is spaced slightly below the upper edge of the fabric layer/post-operative device 525.

A non-adhesive material 523 is applied to the bottom surface of the top piece 520A of the top layer 520 in the neck 528. The material 523 can be made from a polymer film. The material 523 is shown to be generally rectangular and extends upwardly (with reference to FIG. 8A) from the top edge of the bottom piece 520B upwardly into the neck 528 to a point spaced slightly from the top edge of the neck. However, as seen, the material 523 extends to the edge of the notch 529. The material 523 thus effectively covers the adhesive 522 of the top piece 520A in the neck 258, such that the top piece 520A is not adhesively adhered to the fabric layer 514 in the area of the neck. In the area of the neck 528 and below the neck, the top piece 520A is adhered to the bottom piece 520B only in the overlap area 521 and is adhered to the release liner only along an upper margin 527 of the top piece 520A (extending from the upper edge of the material 523 to the upper edge of the neck 528). Thus, the notch, as seen, effectively bisects the material 523. A perforated cut line 558 extends from the bottom of the notch 529 to the bottom of the material 523. This perforated cut line 558 extends through the top piece 520A and the material 523, such that the neck 528 defines tabs T4 to remove the top (perioperative) ply from the fabric (post-operative) ply.

The device 510 is applied to a patient in the same manner as described above, for example, with respect to the device 10. As can be appreciated, the material 523 in the neck will prevent the neck from being adhered to the patient, except for the margins 527 at the top edge and side edge of the neck. Thus, when the medical procedure has been completed, and the practitioner is ready to remove the top ply, the practitioner can slip a finger under the material 523 in top piece in the notch 529. The practitioner can then pull the two halves of the neck 528 in opposite directions, as shown by the arrows A in FIG. 8A. This will start lifting the top piece 520A of the top ply from the patient. As the tabs T4 are pulled in the direction of the arrows A, the adhesive 522 of the top piece 520A in the overlap area 521 will begin lifting bottom piece 520B from the post-operative portion 525. To the extent it may be necessary, the practitioner can rely on the hand hold areas H1 or H2, if necessary, to remove the bottom piece 520B of the top ply from the patient.

The top ply 20, 420A,B, 520A,B (i.e., the perioperative portion) can be made with a film manufactured by 3M under the product number 9865. This film has an elongation rating of 500%. When the device 10, 10' 110, 210 is applied to a patient, the top layer is loaded; however, the loads applied to the top layer are not sufficient to stretch the top layer.

Further, during a surgical procedure, the top layer (perioperative portion) maintains the panniculus in a static or stable position. Post-surgery, after the top layer is removed, the fabric layer (post-operative portion 25, 425, 525) allows for dynamic movement of the panniculus. Thus, the convertible device converts between a perioperative portion which provides for a rigid, stable retraction of the panniculus to a post-operative portion which allows for dynamic motion, which will be more comfortable for the patient.

In use, the complete device 10, 10', 110, 210, 410, 510 is applied to a patient as described above and in our above-noted U.S. Pat. No. 9,427,222 (which description is incorporated herein by reference) to retract a patient's panniculus or other excess tissue during a medical or surgical procedure to enable better access to the treatment site on the patient. During the procedure, the fabric layer will be adhered to the patient by way of the adherent 15, and the fabric layer will be covered with the polyethylene layer. Once the procedure has been completed, the polyethylene layer is removed from the fabric layer using tabs T4 and T5 (if present) to leave only the fabric post-operative device (25, 425, 525) on the patient. In the devices 10, 10', 210, 410, and 510 the post-operative portion is smaller than the perioperative portion. In the device 110, as noted, the entire fabric layer can remain on the patient, to provide a larger post-operative portion. However, the lifting of the top layer can also be used to facilitate removal of the peripheral portion of the fabric layer surrounding the central portion 150, thereby leaving only the smaller central portion 150 to remain on the patient. Thus, the device 110 allows for the option of a post-operative portion that is the same size as the perioperative portion is smaller than the perioperative portion.

Application of the overall device 10, 10', 110, 210, 410, 510 positions the post-operative portion on the patient such that, when the perioperative portion of the device is removed from the patient, the post-operative portion will be in a position to retain the patient's panniculus or other excessive or redundant tissue away from the procedural site to facilitate healing of any wounds or incisions made during the procedure. As such, the device 10, 10', 110, 210, 410, 510 is positioned such that a bottom edge of the fabric layer (of the device 10, 10', 210, 410, 510) or the bottom edge 150b of the central section 150 (of the device 110) is adhered to the panniculus or other excessive or redundant tissue over a large extent of the panniculus and with the top edge at an anchor point on the patient, typically above the panniculus about the xiphoid process.

As can be appreciated, the device 10, 10', 110, 210, 410, 510 is thus convertible between a device which can be applied to a patient prior to a procedure or treatment to maintain the panniculus or other excessive or redundant tissue away from the procedure or treatment site and a device which can be worn for an extended period of time after the procedure or treatment to maintain the panniculus or other excessive or redundant tissue away from the procedure or treatment site to facilitate healing function of any incision, wound, sore, etc. that is present at the procedure or treatment site.

The post-operative portion of the convertible device can remain in its position to support and retain the panniculus away from the medical/surgical site to facilitate healing of medical/surgical site.

As is therefore apparent, the device 10, 10', 110, 210, 410, 510 is used as supplied in the first, or perioperative, phase. That is, the device is applied to the patient to retract the excess and/or redundant tissue (such as the patient's panniculus). In the second, or post-operative, phase, the top layer (perioperative portion) is removed from the fabric layer to convert the device to a wound exposure device, to facilitate healing of the wound (such as a surgical incision). Depending on the procedure, the post-operative device may need to be adjusted or repositioned on the patient to accommodate the needs of the patient/clinician. The adherent 15, which adheres the post-operative portion to the patient's skin, allows for the post-operative portion to be lifted from, and reapplied to, the patient's skin (so as to allow for repositioning of the post-operative portion).

To monitor the wound, the device 10, 110, 210, 410, 510 can be provided with monitoring means 70 (FIG. 1) to monitor physiological conditions in the area of the treatment/procedure site. The monitoring means 70 includes at a minimum, a sensor array 72. It can also include a transmitter 74 to transmit signals from the sensor array to a monitoring device (such as a smart phone, tablet, computer, etc.) and/or a recording device 76 which can record the sensor signals for subsequent upload to a monitoring device (such as a smart phone, tablet, computer, etc.). The sensor array which measures physiological effects of the wound can include sensors which detect temperature, humidity, pH of the skin, static/ charge of the device and/or skin, motion, stress to both the patient's skin and the device, tension/stretching of the device or a layer or portion thereof (such as the post-operative or perioperative portions), spectroscopic data indicative of, for example, blood oxidation, pulse rate, etc. The sensor array 72 can include any combination of these sensors. The circuitry for the monitoring means can be woven directly into the fabric layer. Alternatively, the circuitry can be printed on the fabric layer. In the latter instance, the circuitry would be printed using known printing techniques.

The sensing means 70 is located in the area of the post-operative portion, so that it stays with the post-operative portion when the perioperative portion is removed. Further, the sensing means 70 is positioned in the post-operative portion such that the sensor array 72 is in sensing relationship with the area of the patient (i.e., proximate the area of the wound) when the device is applied to, and worn by, the patient. The sensing means is illustratively shown in FIG. 1 to be proximate the cross-cut 36 which is one-quarter to one-third of the way up from the bottom edge of the post-operative portion and in the approximate middle of the post-operative portion. As can be appreciated, the sensing means 70 could be positioned in most any desired location of the post-operative portion.

In use, the sensor array 72 will issue signals indicative of the physiological condition(s) being monitored. The signals are stored in the recording device 76 and/or are transmitted using the transmitter 74 to, or read by, a receiving device. If the sensor array has transmitting capabilities, the receiving device can be a smart phone, tablet, computer, etc. On the other hand, if the signals are stored in the recording device, then the recording device can be, for example, an RFID tag, and the receiving device can be a reader which can read the receiving device. Preferably, the recording device is small and/or flexible, such that it will not interfere with either the use (placement) of the device or the comfort of the patient when worn long term. The receiving device can be provided with a logic circuit (i.e., an app) that interprets or analyzes (or executes programming instructions which interpret or analyze) the signals and determines if any of the monitored parameters fall outside of a desired range. If the parameter does fall outside of a desired range, the receiving device can issue an alarm (which can be auditory, visual, or tactile). Such parameters can be thermal and/or photo-spectroscopic indicating (i.e., that they can be sensed or monitored thermally or photo-spectroscopically).

In addition, any of the devices can be provided with a port and or a port assembly 80 located in the post-operative portion. The port assembly is shown schematically in FIGS. 1 and 4, but can be applied to any of the convertible devices described herein. Such a port assembly can be as disclosed in US Pub No. 20180110659, which is incorporated herein by reference. The port assembly 80 can comprise a cannula, comprising a tube 82, that is connectable to a pressure or vacuum source. The tube 82 extends upwardly from a base or flange 84, the top of which is adhered to the bottom of the adherent 15. As seen in FIG. 1, the base or flange 84 defines a propeller shape having three lobes extending from a central section of the base. A typical wound dressing 86, having an area greater than the area defined by the base 84, covers the bottom of the base or flange 84. The top of the wound dressing 86 engages, and is adhered to, the adherent (except where the top of the wound dressing 86 engages the bottom of the base 84). The port tube 82 is hollow, and is open at its top (to be connected to a pressure of vacuum source) and opens at the wound dressing 86. The wound dressing 86 is preferably made from a material which will facilitate the flow of gases and liquids. As can be appreciated, the wound dressing 86 will be in contact with the patient's skin and will thus prevent the base or flange 84 from impinging on the patient, which could potentially cause discomfort to the patient. If the tube 82 is connected to a vacuum source, then the port assembly 80 can facilitate drainage of a wound if the port, and particularly the wound dressing, is positioned over the wound. The port, on the other hand, provides an opening, or an openable area in the post-operative portion where a port assembly can be added to the adhesive device prior to application of the device to a patient. In this instance, the device, as manufactured, would not include the port assembly.

As various changes could be made in the above constructions without departing from the scope of the invention, it is intended that all matter contained in the above description or shown in the accompanying drawings shall be interpreted as illustrative and not in a limiting sense.

The invention claimed is:

1. A convertible adhesive device for repositioning and stabilizing excessive and/or redundant tissue prior to a medical/surgical procedure and for maintaining the excessive and/or redundant tissue away from a wound site after the medical/surgical procedure; the convertible adhesive device comprising a perioperative portion, a post-operative portion, and a release liner:
    said perioperative portion having an upper surface and a lower surface, and comprising a top layer; the perioperative portion having an elongation factor less than an elongation factor of said post-operative portion;
    said post-operative portion having an upper surface and a lower surface; said post-operative portion defining an area smaller than an area of said perioperative potion, such that a margin is defined between edges of said post-operative portion and said peri-operative portion;
    wherein the perioperative portion is removably adhered to the upper surface of the post-operative portion by means of an adhesive; and the release liner is removably adhered to the lower surface of at least the post-operative portion by means of an adherent, said adherent comprising a silicone gel, an acrylate adhesive, or both; said adhesive holding said perioperative portion to said post-operative portion being weaker than said adherent;
    wherein the perioperative portion includes at least one separable line, at least a part of which overlies said post-operative portion, and at least one pull tab proximate said at least one separable line, said at least one pull tab being positioned within and spaced interiorly of the edges of the post-operative portion, said at least one pull tab comprising an adhered portion secured to said perioperative portion and a grasping portion, said adhered portion being positioned on one side of said at least one separable line and said grasping portion positioned at least in part on an opposite side of said at least one separable line; whereby, when said pull tab is pulled, said perioperative portion will be removed from said post-operative portion.

2. The convertible adhesive device of claim 1 wherein said adherent covers substantially the entire bottom surface of said post-operative portion.

3. The convertible adhesive device of claim 1 wherein the adherent comprises a silicone gel.

4. The convertible adhesive device of claim 1 wherein said lower surface of said perioperative portion is substantially covered with said adhesive to removably secure said perioperative portion to at least said upper surface of said post-operative portion.

5. The convertible adhesive device of claim 4 wherein said adhesive is an acrylate adhesive or coadhesive.

6. The convertible adhesive device of claim 1 wherein the post-operative portion is comprised of a knit fabric or a woven fabric.

7. The convertible adhesive device of claim 1 wherein the post-operative portion is a nylon fabric.

8. The convertible adhesive device of claim 7 wherein said post-operative portion has a through-cut; said through-cut defining a periphery of a central portion of said post-operative portion; whereby a margin is formed between the periphery of said central portion and edges of said post-operative portion.

9. The convertible adhesive device of claim 1 wherein said perioperative portion lower surface has a second adhesive thereon; said release liner being removably adhered to said perioperative portion in said margin; said margin being adapted to be adhered to a patient during use.

10. The convertible adhesive device of claim 1 wherein said separable line is a perforated line and wherein said pull tab is a first pull tab; said convertible adhesive device including at least one second pull tab; said second pull tab having a secured portion adhered to the top surface of said top layer on a second side of said perforated line and a grasping portion; said secured portion having a first end proximate said perforated line and a distal end remote from said perforated line; said grasping portion extending from said first end of said secured portion; whereby said second tab is oriented in a direction opposite said first tab.

11. The convertible adhesive device of claim 10 wherein said perforated line is a kiss-cut and is generally bell-shaped.

12. The convertible adhesive device of claim 11 including a second perforated line, said second perforated line extending through a cross portion of said generally bell-shaped perforated line.

13. The convertible adhesive device of claim 1 wherein said convertible adhesive device further includes at least one port and/or a port assembly and flanged cannula positioned in said post-operative portion; said port assembly comprising a hollow tube passing through said post-operative portion; said hollow tube being adapted to be connected to a vacuum or pressure source.

14. The convertible adhesive device of claim 13 wherein said convertible adhesive device includes a wound dressing below said hollow tube; said wound dressing being positioned to be between said a patient and said tube when said convertible adhesive device is applied to a patient.

15. The convertible adhesive device of claim 1, wherein the convertible adhesive device is a multi-ply device and the layers or plies thereof are comprised of a combination of materials formulated from monomers, polymers and co-polymers to construct the desired layers.

16. The convertible adhesive device of claim 1, wherein, the device is adapted to induce loading in the post-operative device upon removal of the perioperative portion, and wherein the post-operative portion is adapted to be adjusted and loaded to accommodate the need of a patient/clinician.

17. An adhesive convertible tissue stabilizer that relieves compression at or adjacent to an incision or a wound site while minimizing movement of the wound margins to improve healing; said adhesive convertible tissue stabilizer comprising the convertible adhesive device of claim 1, wherein the silicone gel is a coadhesive silicone gel.

18. A method of converting the convertible adhesive device of claim 1 from a perioperative panniculus retractor that was applied aseptically to a patient prior to a medical/surgical procedure to a post-operative panniculus retractor; said method comprising, after said convertible adhesive device has been applied to a patient, removing said perioperative portion from said post-operative portion while said post-operative portion is adhered to said patient.

19. The method of claim 18 wherein said post-operative portion can be removed from, and reapplied to, said patient.

20. The method of claim 18 wherein said post-operative portion can be worn by said patient for at least ten days.

21. The method of claim 18 wherein the post-operative portion is located adjacent to an incision.

* * * * *